(12) United States Patent
Amamiya et al.

(10) Patent No.: US 7,916,285 B2
(45) Date of Patent: Mar. 29, 2011

(54) REFRACTOMETER

(75) Inventors: Hideyuki Amamiya, Tokyo (JP);
Yoshinori Nakashima, Tokyo (JP);
Kiminori Sekiguchi, Tokyo (JP);
Junichi Matsumoto, Tokyo (JP);
Yoshiaki Torigoe, Tokyo (JP)

(73) Assignee: Atago Co., Ltd. (JP)

( * ) Notice: Subject to any disclaimer, the term of this patent is extended or adjusted under 35 U.S.C. 154(b) by 131 days.

(21) Appl. No.: 12/191,024

(22) Filed: Aug. 13, 2008

(65) Prior Publication Data
US 2009/0046277 A1 Feb. 19, 2009

(30) Foreign Application Priority Data

Aug. 13, 2007 (JP) .................................. 2007-210895

(51) Int. Cl.
*G01N 21/41* (2006.01)
(52) U.S. Cl. ...................................... 356/128; 356/135
(58) Field of Classification Search ........... 356/128–137
See application file for complete search history.

(56) References Cited

U.S. PATENT DOCUMENTS

| | | | | |
|---|---|---|---|---|
| 3,628,867 A * | 12/1971 | Brady | | 356/136 |
| 3,770,352 A * | 11/1973 | White | | 356/133 |
| 4,381,895 A * | 5/1983 | Hughes et al. | | 356/134 |
| 4,692,024 A * | 9/1987 | Bloss | | 356/135 |
| 4,704,029 A * | 11/1987 | Van Heuvelen | | 356/39 |
| 5,064,619 A * | 11/1991 | Finlan | | 422/82.05 |
| 5,822,073 A * | 10/1998 | Yee et al. | | 356/445 |
| 5,898,503 A * | 4/1999 | Keller et al. | | 356/445 |
| 5,973,774 A * | 10/1999 | Haggett et al. | | 356/135 |
| 6,195,160 B1 * | 2/2001 | Rainer et al. | | 356/135 |
| 6,396,576 B1 * | 5/2002 | Bleyle | | 356/128 |
| 6,707,542 B1 * | 3/2004 | Cotton et al. | | 356/136 |
| 6,798,521 B2 * | 9/2004 | Elkind et al. | | 356/445 |
| 7,369,221 B2 * | 5/2008 | Amamiya et al. | | 356/135 |

* cited by examiner

*Primary Examiner* — Sang Nguyen
(74) *Attorney, Agent, or Firm* — McAndrews, Held & Malloy, Ltd.

(57) ABSTRACT

Certain embodiments of the present invention provide a refractometer including: a housing having an immersion portion, the immersion portion having an opening; a light source for emitting a light; a light sensor for converting a received light into an electrical signal; a prism including faces, including: a first face proximal to the light source and the light sensor; a second face, at least a portion of the second face configured for contacting a sample liquid through the opening, and for forming an interface between the second face and the sample liquid; and a third face, wherein the light travels by: being directed towards the second face; being reflected at least in part by the interface towards the third face; and being reflected at least in part by the third face towards the light sensor. In an embodiment, the refractometer further includes a control portion for receiving the electrical signal, and for determining a refractive index of the sample liquid based at least in part on the electrical signal. In an embodiment, the control portion determines the refractive index in at least one of: a batch mode for detecting the electrical signal once; and a sequential mode for detecting the electrical signal at least twice. In an embodiment, the refractometer further includes a substrate at least partially positioned within the housing, the substrate supporting the light source and the light sensor. In an embodiment, the refractometer further includes a display portion connected to the control portion for displaying a representation of the refractive index.

18 Claims, 8 Drawing Sheets

REFRACTOMETER

CROSS-REFERENCE TO RELATED APPLICATIONS/INCORPORATION BY REFERENCE

This patent application makes reference to, claims priority to and claims benefit from Japanese Patent Application No. 2007-210895, filed Aug. 13, 2007.

BACKGROUND OF THE INVENTION

Embodiments of the present application relate generally to a refractometer. Particularly, certain embodiments relate to a refractometer for measuring the content of solute in a liquid.

Figure 8:
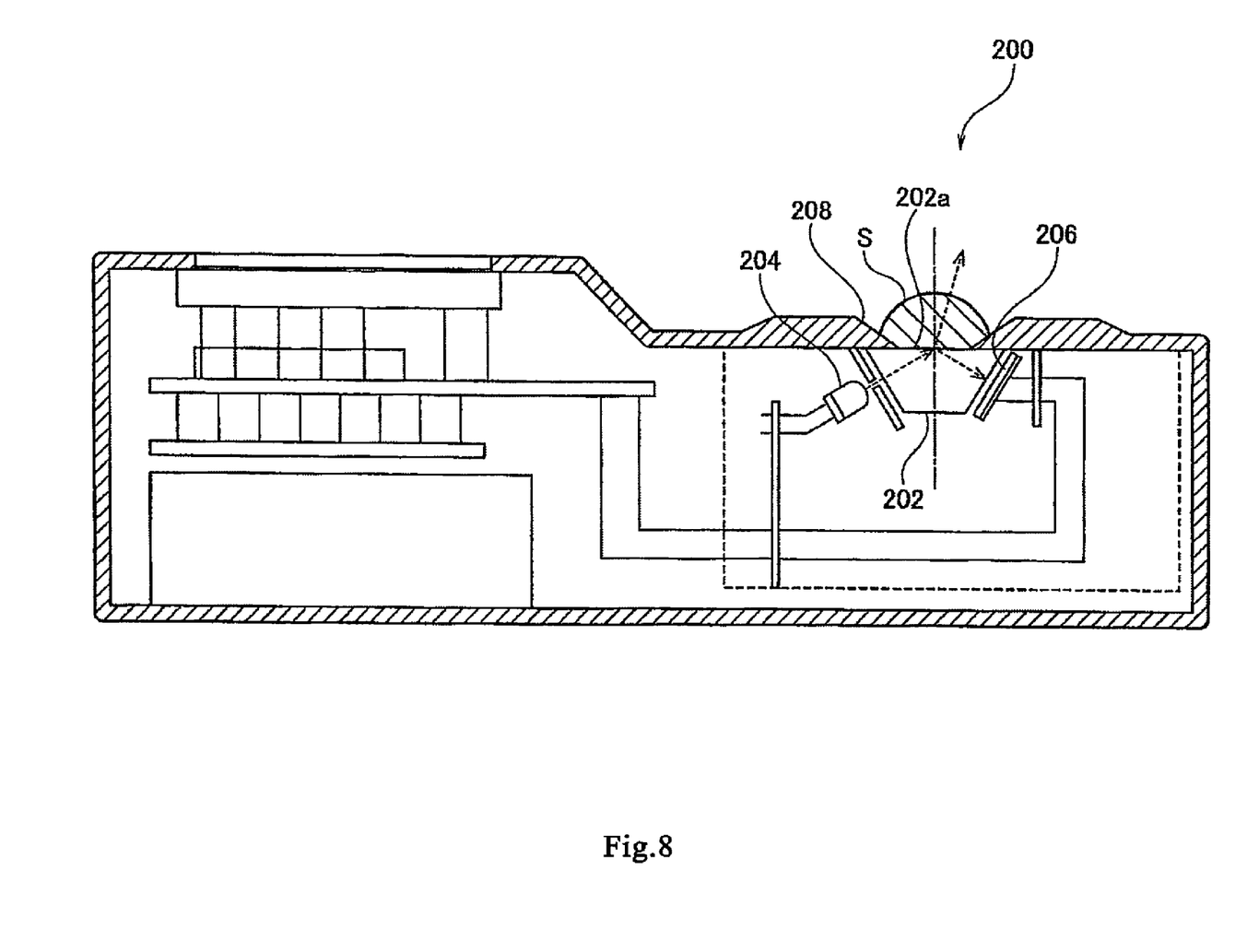
FIG. 8 shows a prior art refractometer.

Referring to FIG. 8 (taken from Japanese Patent Gazette No. 2004-150923), a digital refractometer 200 is shown. The refractometer has a prism 202, a light source 204, and a light-receiving sensor 206. The light source 204 projects light to the interface between a sample liquid S and the prism 202. Light is reflected from the interface at an angle determined by the index of refraction of the sample liquid S. The reflected light is received by the light-receiving sensor 206 and converted to an electrical signal. From this signal, it may be possible to determine the refractive index of the liquid. Since the refractive index of a liquid is related to the content of the substance dissolving in the liquid, refractometers can be used as a tool for measuring the concentration of soluble substance in a liquid—e.g. as a saccharometer for measuring sugar content. Such devices may be used to evaluate the sugar content of grocery produce, for example.

The refractometer 200 is designed in such a way that the sample liquid S is to be dripped on the prism 202 for measurement. However, the refractometer 200 may not function effectively if it is immersed in the sample liquid S. Furthermore, since the face 202a of the prism 202 that touches the sample liquid S is deeper than the sample stable 208 surrounding the face 202a, the refractometer 200 may be unable to function effectively when the prism 202 is brought in contact with a part of a piece of grocery produce, such as the cross-section of an orange.

Thus, there is a need for a refractometer capable of measuring a refractive index of a liquid when immersed at least partially in the liquid. Further, there is a need for a refractometer to operate by touching or bringing it into contact with a liquid bearing item, such as grocery produce.

BRIEF SUMMARY OF THE INVENTION

Certain embodiments of the present invention provides a refractometer including: a housing having an immersion portion, the immersion portion having an opening; a light source for emitting a light; a light sensor for converting a received light into an electrical signal; a prism including faces, including: a first face proximal to the light source and the light sensor; a second face, at least a portion of the second face configured for contacting a sample liquid through the opening, and for forming an interface between the second face and the sample liquid; and a third face, wherein the light travels by: being directed towards the second face; being reflected at least in part by the interface towards the third face; and being reflected at least in part by the third face towards the light sensor. In an embodiment, the immersion portion includes a corrosion resistance material. In an embodiment, the corrosion resistance material includes stainless steel. In an embodiment, the immersion portion includes a surface substantially surrounding the opening, the surface being substantially in a same plane as the second face. In an embodiment, the first and second faces is approximately between 25 to 45 degrees. In an embodiment, an angle between the first and third faces is approximately between 15 to 60 degrees. In an embodiment, an angle between the second and third faces is approximately between 95 to 120 degrees. In an embodiment, the refractometer further includes a control portion for receiving the electrical signal, and for determining a refractive index of the sample liquid based at least in part on the electrical signal. In an embodiment, the control portion determines the refractive index in at least one of: a batch mode for detecting the electrical signal once; and a sequential mode for detecting the electrical signal at least twice. In an embodiment, the refractometer further includes a substrate at least partially positioned within the housing, the substrate supporting the light source and the light sensor. In an embodiment, the refractometer further includes a display portion connected to the control portion for displaying a representation of the refractive index.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings. Further, some figures may be representations of the type of display and/or output associated with methods and systems of the present invention, in accordance with one or more embodiments.

DETAILED DESCRIPTION OF THE INVENTION

Figure 1:
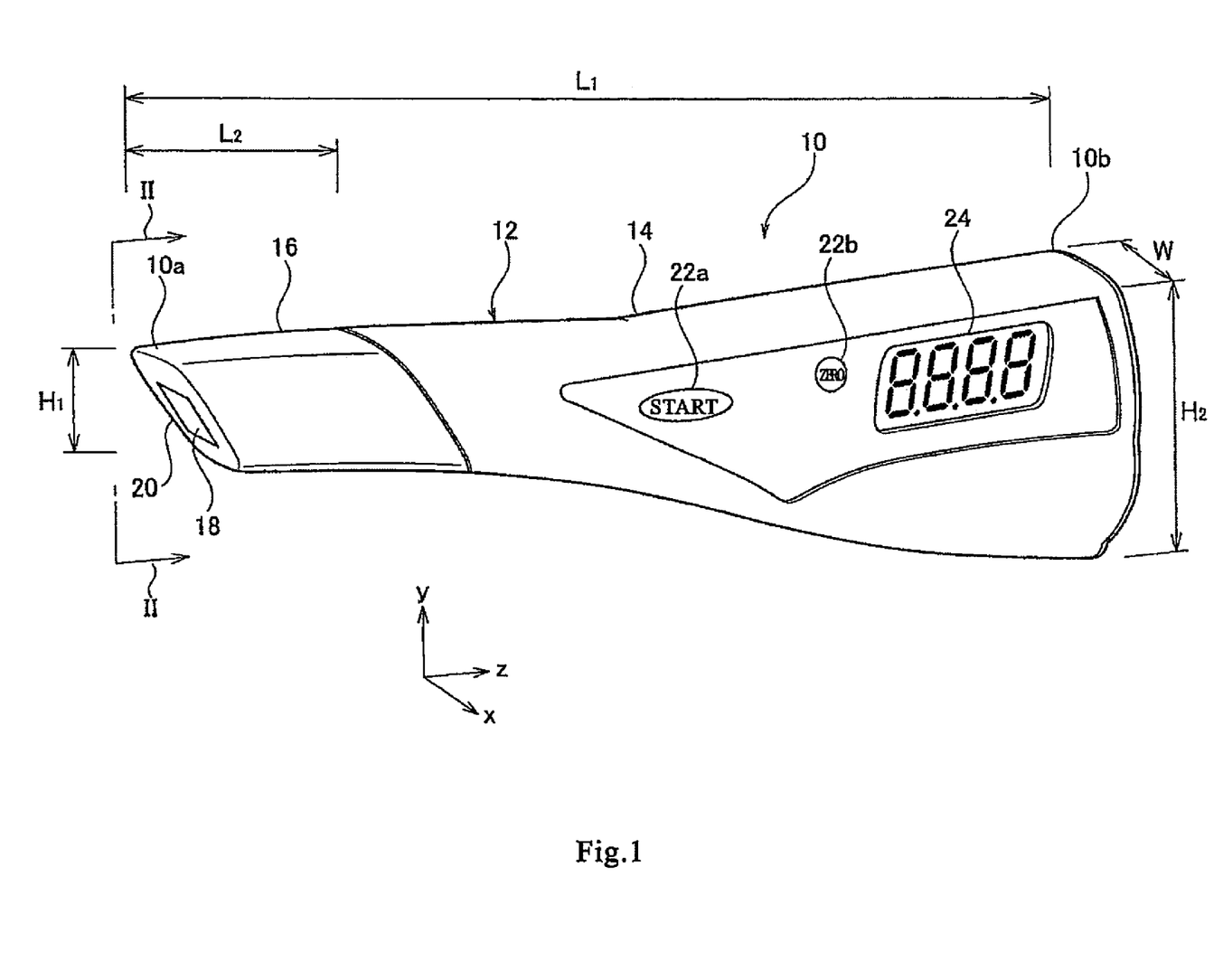
FIG. 1 shows a perspective view of a refractometer, according to an embodiment of the present invention.

FIG. 1 shows a perspective view of a refractometer 10, according to an embodiment of the present invention. The refractometer 10 may have an elongated shape, generally. For example, the height of the refractometer 10 measured along y direction may become larger from a first end 10a (H1) to a second end 10b (H2).

Figure 2:
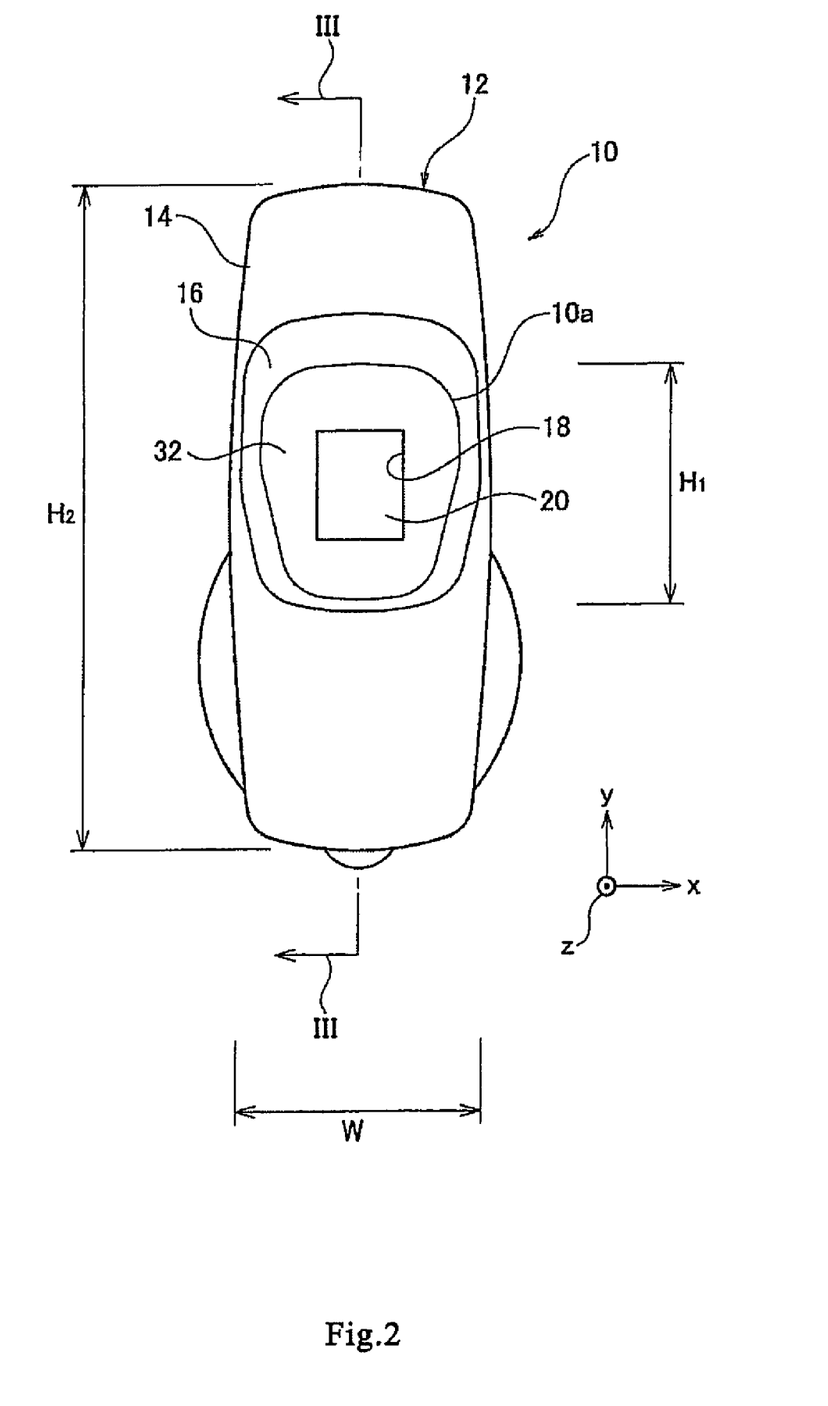
FIG. 2 shows a side view of a refractometer, according to an embodiment of the present invention.

FIG. 2 shows a side view of a refractometer, according to an embodiment of the present invention. As shown, the width of the refractometer 10 measured along x direction may be substantially constant. Hereinafter, the length direction of the refractometer is referred to as the z direction, height as y direction, and width as x direction. In an embodiment, the length L1 of the refractometer is approximately 80-120 mm.

In an embodiment, the height H1 of the first end of the refractometer 10a is approximately 7-18 mm. In an embodiment, the height H2 of the second end of the refractometer 10b is approximately 7-40 mm. In an embodiment, the width W of the refractometer is 5~20 mm. In such a way, the refractometer 10 may be held in hand like a pen.

Referring again to FIG. 1, the housing 12 of the refractometer 10 comprises a main body 14 and an immersion portion 16 which may be immersed in a sample liquid. The immersion portion 16 may be disposed on the side of the first end of the refractometer 10a. The immersion portion 16 may have an elongated shape. In an embodiment, the length L2 of the immersion portion 16 along the z direction is preferably approximately 5-150 mm. The front end of the immersion portion 16 may have an opening 18 for accommodating a prism 20 for touching the sample liquid. The immersion portion 16 may comprise a drug-resistance material such as PBT resin (polybutylene terephthalate) and ABS resin (acrylonitrile-butadiene-styrene), or a corrosion resistance material such as stainless steel, or aluminum or zinc castings coated with Ni, NiCr, PTFE (polytetrafluoroethylene) or the like. In an embodiment, the immersion portion 16 is made of an austenitic stainless steel such as SUS316. With such a material, the immersion portion 16 may be immersed in a corrosive liquid, such as citrus juice (e.g., lemon or orange), vinegar, saline solution, soybean sauce, oil or the like.

Figure 6:
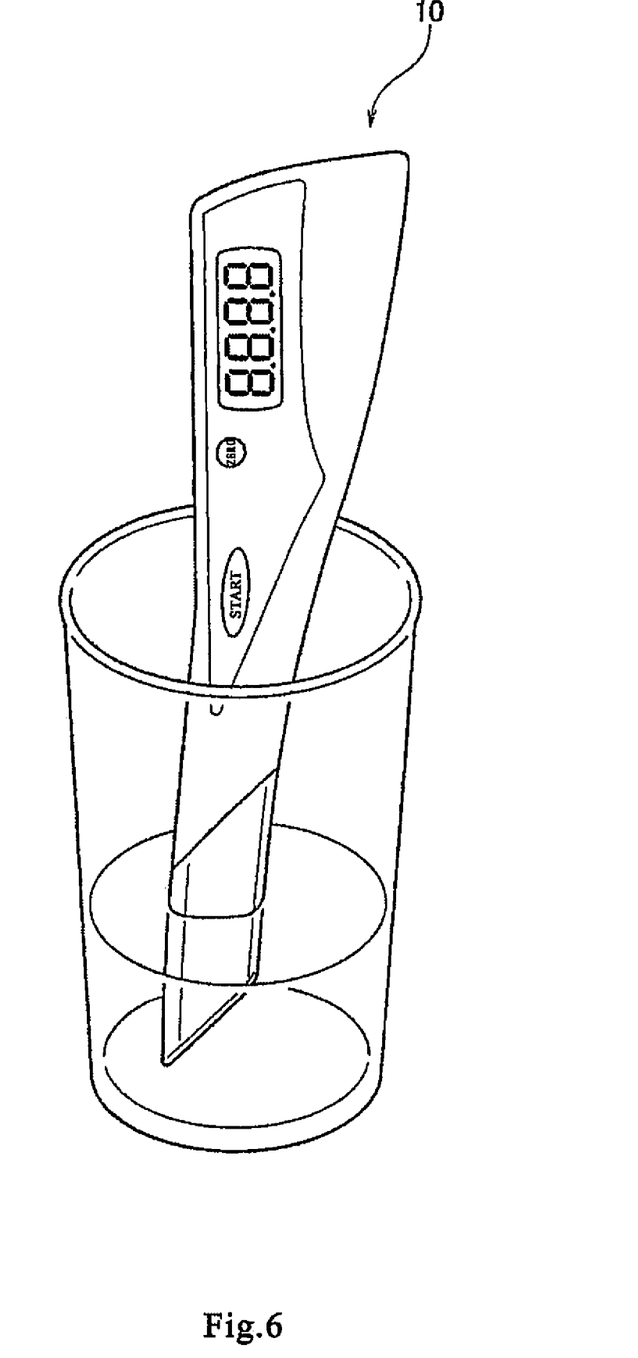
FIG. 6 shows a refractometer immersed in a sample liquid, according to an embodiment of the present invention.

The refractometer 10 may have, on the main body 14, operation portions 22a and 22b, which may initiate the refractometer 10 to measure the sample liquid and to reset the refractometer 10. The refractometer may further have a display portion 24 for displaying a representation of the measured refractive index. A display portion 24 may comprise a liquid crystal display or the like. The main body 14 may comprise a thermoplastic resin, such as ABS resin. Consequently, the refractometer 10 may not sink when immersed into a container such as a cup (as shown in FIG. 6), if the center of gravity of the refractometer is located in the immersion portion 16 made of stainless steel, for example.

Figure 3:
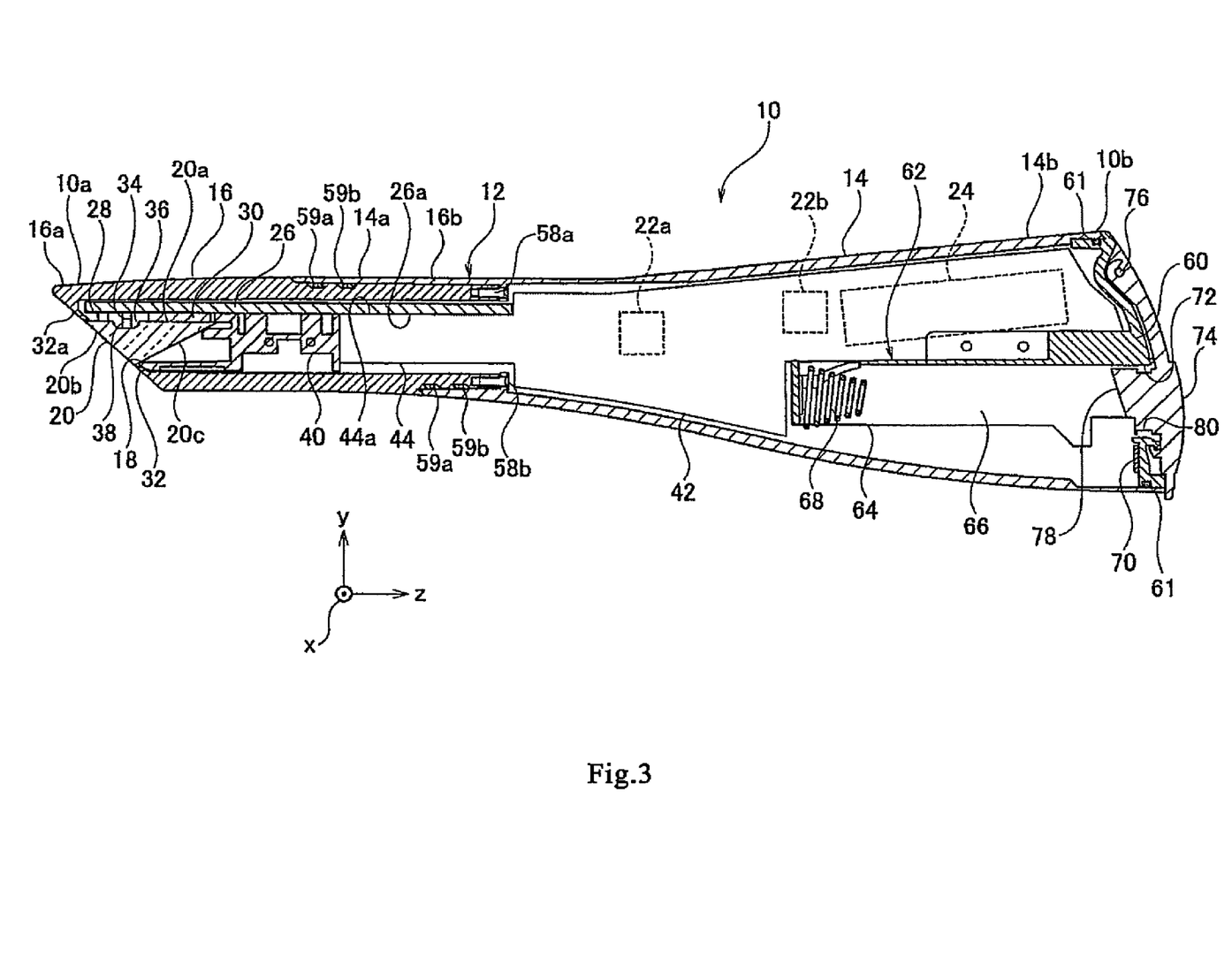
FIG. 3 shows a cross-section of a refractometer, according to an embodiment of the present invention.

FIG. 3 shows a cross-section of a refractometer, according to an embodiment of the present invention. The refractometer may have a first substrate 26 extending on the zx plane. The first substrate 26 may be positioned at least in part within the immersion portion 16. The first substrate 26 may be disposed on the side of the first end portion 10a of the refractometer 10, e.g., on the side of the front end of the immersion portion 16. The first substrate 26 may support a light source 28 and a light sensor 30. The first substrate 26 may also support a prism 20.

Figure 4:
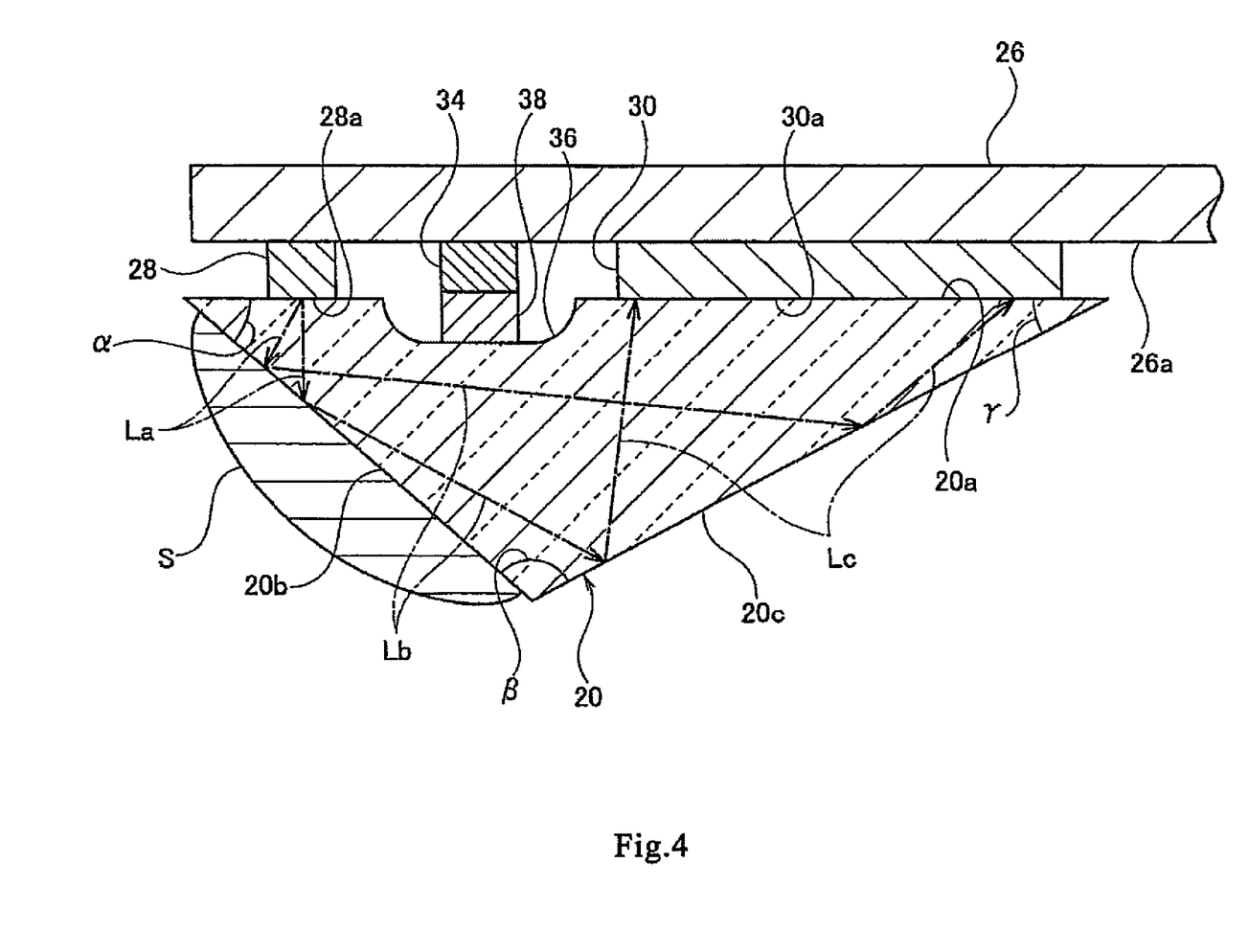
FIG. 4 shows a cross-section of an immersion portion of a refractometer, according to an embodiment of the present invention.

FIG. 4 shows a cross-section of an immersion portion of a refractometer, according to an embodiment of the present invention. The light source 28 and the light sensor 30 may be affixed on the same surface 26a of the first substrate 26. For example, the light source 28 and the light sensor 30 may be spaced along the z direction, where the light source 28 is closer to the front end of the immersion portion 16 (see, e.g., FIG. 3).

The light source 28 is may be a light emitting diode (LED). For example, a surface-mounted LED assembly having dimensions of 1.6 mm (length)×0.8 mm (width)×0.45 mm (height) may be used as the light source 28. The light sensor 30 may be a one-dimension image sensor, such as a charge coupled device (CCD) or a complementary metal-oxide semiconductor (CMOS). For example, a CCD linear image sensor having a dimension of 1.0 mm (length)×8.8 mm (width)×0.645 mm (height) may be used as the light sensor 30.

A first face 20a of the prism 20 may be configured proximal to the light emitting surface 28a of the light source 28 and the light-receiving surface 30a of the light sensor 30. The prism 20 may be spaced from the surface 26a of the first substrate 26 by approximately 1.0-1.5 mm, for example. By positioning the light source 28 and the light sensor 30 on the surface 26a of the substrate 26 and facing to the first face 20a of the prism 20, the surrounding space of the prism 20 may be reduced. In such a configuration, the immersion portion 16 may be reduced, thus allowing for a compact refractometer 10.

Referring again to FIG. 3, the second face 20b of the prism 20 may be positioned towards the opening 18 disposed on the wall 32 of the front end 16a of the immersion portion 16. The prism 20 may be coupled to the opening 18 through the surrounding portion of the second face 20b. The second face 20b may be exposed through the opening 18, and configured to come in contact with the sample liquid to an interface between the second face 20b and the sample liquid. The second face 20b may be substantially in the same plane as the outer surface 32a of the wall 32 surrounding the opening 18. In such a configuration, the second face 20b may be brought in contact with the cross-section of a fruit for measurement, for example.

Referring to FIG. 4 again, the third face 20c of the prism 20 may reflect light emitted from the light source 28 and further reflected by the interface between the prism 20 and the sample liquid S. The light reflected by the third face 20c may be directed onto the light-receiving surface 30a of the light sensor 30. For example, the light source 28 may emit a light La incident to the second face 20b. The interface formed by the second face 20b and the sample liquid has an index of refraction. According to the index of refraction of the sample liquid S and the prism 20, the light La is separated into a refracted light beam and a reflected light beam Lb. The reflected light beam Lb is incident to the third face 20c. The third face 20c reflects the reflected light beam Lb from the second face 20b to the light-receiving surface 30a of the light sensor 30. Again, the light source 28 and light sensor 30 may be disposed on the same substrate, and/or may be positioned proximal to the first face 20a. The third face 20c may function as a reflector, in place of a separate device, such as light guide, mirror and lens, for example.

The angles $\alpha$, $\beta$ and $\gamma$ among the three faces 20a, 20b and 20c may be selected with consideration of various factors. For example, the angles may be selected based on: the refractive index of the prism 20; a desired measuring range of refractive index; and/or the reflection of the light from the second face 20b by the third face 20c. Furthermore, the dimensions of the faces 20a, 20b and 20c may be determined by various factors, including the dimension of the light sensor 30, and/or the preferred resolution.

The refractive index of the prism 20 may be selected based on the estimated characteristics of the sample liquid. For example, the refractive index of the prism 20 may be approximately 1.4-2.4. When, for example, the refractive index of the prism 20 is 1.6 and the measuring range is approximately 1.33-1.55, the angles may be selected as follows: angle $\alpha$ may be approximately 25-45 degrees; angle $\beta$ gamma may be approximately 95-120 degrees; and angle $\gamma$ may be approximately 15-60 degrees.

A temperature sensor 34 may be configured on the face 26a of the first substrate 26 between the light source 28 and the light sensor 30. The temperature sensor 34 may comprises a platinum film temperature sensor, for example. Such a platinum film temperature sensor may have dimensions of 1.6 mm (length)×0.8 mm (width)×0.45 mm (height).

Furthermore, a recess 36 may be provided on the first face 20a of the prism 20 facing the temperature sensor 34. A heat conductive portion 38 may be arranged in the recess 36 for thermally coupling the temperature sensor 34 and the prism 20. The heat conductive portion 38 is may comprise heat conductive rubber, for example.

Referring to FIG. 3 again, an optical chassis 40 may be provided on the surface 26a of the first substrate 26 to support the prism 20. The chassis 40 may also shield the light source 28, the light sensor 30 and/or the prism 20 from scattered light. The optical chassis 40 may comprise a thermoplastic resin such as polycarbonate (PC), acrylonitrile-butadiene-styrene (ABS) resin, polyphenylene ether (PPE) resin or the like.

A second substrate 42 may be coupled to the first substrate 26 at the end of the base 16b of the immersion portion. Operation portions 22a and 22b, a display portion 24 and a control portion 46 may be supported on the second substrate 42. The second substrate 42 may extend along the yz plane within the main body 14, and may substantially form a right angle with the first substrate 26 extending along the zx plane. For example, a side face 44a of an extension portion 44 of the second substrate 42 extending within the immersion portion 16 and the surface 26a of the first substrate 26 may form a T-shape arrangement, and may be connected by soldering, such as soft soldering. In such a way, electrical conduction between the first substrate 26 and the second substrate 42 may be wireless.

Figure 5:
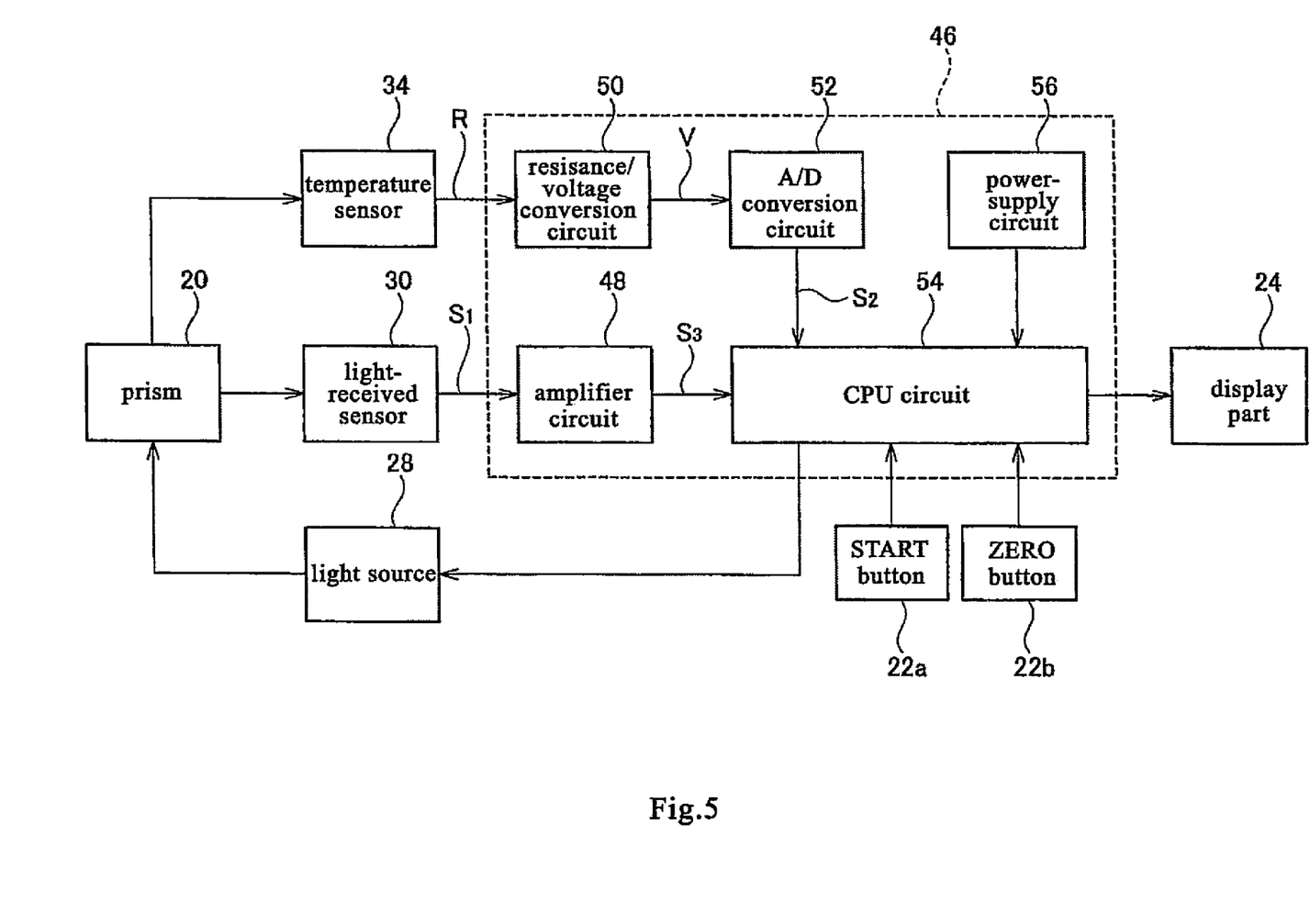
FIG. 5 shows a block diagram of a refractometer, according to an embodiment of the present invention.

FIG. 5 shows a block diagram of a refractometer, according to an embodiment of the present invention. The control portion 46 may include an amplifier circuit 48 connected with the light sensor 30, a resistance/voltage conversion circuit 50 connected with the temperature sensor 34, an A/D conversion circuit 52 connected with the resistance/voltage conversion circuit 50, a CPU circuit (e.g., calculator) 54 connected with the amplifier circuit 48 and the A/D conversion circuit 52, and a power-supply circuit 56 connected with the CPU circuit 54, for example. The power-supply circuit 56 may supply power to the CPU circuit 54 and other circuits, such as the light source 28 and the display portion 24, for example.

The amplifier circuit 48 may amplify the electrical signal S1 output from the light sensor 30. The resistance/voltage conversion circuit 50 may convert the resistance value R output by the temperature sensor 34 into a voltage value V. The A/D conversion circuit 52 may convert the voltage value V output by the resistance/voltage conversion circuit 50 into a digital signal S2.

The CPU circuit 54 may have a memory (not shown) which stores a program for converting the electrical signal S3 output by the amplifier circuit 48 into a concentration value and a program for converting the digital signal S2 output from A/D conversion circuit 52 into a temperature compensation value.

Furthermore, the CPU circuit 54 may have a memory (not shown) which is connected to a START button 22a and a ZERO button 22b of the operation portion, and which stores a program which runs when the ZERO button 22b is activated for correction, for example. The CPU circuit 54 may have a further memory (not shown) which stores program for selectively executing any one of a batch detecting mode in which only one detection is made when the START button 22a is pressed and a sequential detecting mode (for example, one detection per 5 seconds and 60 detections in total) in which sequential multiple detections are made when the START button 22a is pressed. The detecting mode may be switched by, for example, pressing the START button 22a and the ZERO button 22b at the same time.

Referring to FIG. 3 again, the main body 14 of the housing 12 and the immersion portion 16 may be engaged into the first end 14a of the main body 14 through the base 16b of the immersion portion 16 and then jointed together. The main body 14 may further connect to the immersion portion 16 by screws 58a and 58b or the like. O-shape rings 59a and 59b may be configured at the joint portion of the main body 14 and the immersion portion 16.

The housing 12 may have a cap 60 engaged with the second end 14b of the main body 14. Similar to the main body 14, the cap 60 may comprise a thermoplastic resin, such as ABS resin. An O-shape ring 61 may be provided at the joint portion of the main body 14 and the cap 60.

A battery storage portion 62 may be provided at the second end 10b of the refractometer 10 for storing a battery. The battery storage portion 62 comprises a battery chamber 66 with a partition 64 rested on the second substrate 42, and a first contact 68 and a second contact 70 configured in the battery chamber 66 and electrically connected to the power-supply circuit 56 (as shown in FIG. 5). The battery chamber 66 may have an opening 72 disposed on the cap 60 for loading/unloading battery.

The battery storage portion 62 further may have a battery cover 74 for opening/closing the opening 72. The battery cover 74 may be rotatably or slidably mounted on the cap 60 through a pin 76, for example. The battery cover 74 may have a protrusion 78 engaged with the opening 72. An annular groove 80 may be provided on the peripheral of the protrusion 78, and a gasket (not shown) may be disposed in the annular groove 80. The battery cover 74 may be made of elastic material such as a thermoplastic elastomer, PP resin (polypropylene) or the like. The gasket may be made of ethylene-propylene-diene monomer (EPDM).

As an illustration, the refractometer 10 may operate in the following manner. When the prism 20 is brought in contact with the sample liquid and the START button 22a is pressed, the light source 28 may begin emitting light. The light incident to the prism 20 emitted from the light source 28 is separated into a refracted light beam and a reflected light beam on the interface between the sample liquid and the prism 20 according the critical angle of total reflection defined by the relative refractive index of the sample liquid and the prism 20. The reflected light beam is reflected by the third face 20c of the prism 20, thus imaging on the light sensor 30 and converted into an electrical signal S1 by the light sensor 30. The electrical signal is then amplified by the amplifier circuit 48 and sent to the CPU circuit 54.

The temperature sensor 34 detects the temperature of the prism 20 and outputs a resistance value R corresponding to the temperature value. The resistance value R is converted by the resistance/voltage conversion circuit 50 into a voltage value V, and is further converted by the A/D conversion circuit 52 into a digital signal S2 which is sent to the CPU circuit 54.

In the CPU circuit 54, a refractive index is determined according to the electrical signal S3 output by the amplifier circuit 48. The refractive index is then compensated with the digital signal S2 output by the A/D conversion circuit 52, so as to produce a value of concentration such as sugar content which is displayed on the display portion 24.

As an illustration, the refractometer 10 may be manufactured as follows. A recess 36 is formed on the prism 20, and the three faces 20a, 20b and 20c are ground. Wiring is formed on the first and second substrates 26 and 42. The CPU circuit 54 and other circuits, the START button 22a and the ZERO button 22b, and the display portion 24 and the like are disposed on the second substrate 42.

The light source 28, the light sensor 30 and the temperature sensor 34 are fixed on the face 26a of the first substrate 26, as shown in FIG. 4. Next, after the heat conductive portion 38 is configured in the recess 36 of the prism 20, the optical chassis 40 for supporting the prism 20 is fixed onto the first substrate 26 through a connection portion such as screws. As a result, the first face 20a of the prism 20 is configured facing the light-emitting surface 28a of the light source 28 and the light-receiving surface 30a of the light-receiving sensor 30.

The side face 44a of the extension portion 44 of the second substrate 42 is rested against the surface 26a of the first substrate 26. The second substrate 42 is connected to the optical chassis 40 through a connection portion such as screws, and is joined to the first substrate 26 by soft soldering. In such a way, wiring of the first substrate 26 and the second substrate 42 is connected, and the light source 28, the light-receiving sensor 30 and the temperature sensor 34 on the first substrate 26 are connected to the CPU circuit 54 and other circuits on the second substrate 42.

The main body 14 and the cap 60 are formed through injection molding with a thermoplastic resin such as ABS resin. The immersion portion 16 is molded with stainless steel through metal molding method or the like. The battery cover 74 of the battery storage portion 62, molded by a thermoplastic elastomer, is mounted on the cap 60.

The base 16a of the immersion portion 16 is engaged into the first end 14a of the main body 14. Then the tool is inserted from the side of second end 14b of the main body 14, the main portion 14 and the immersion portion 16 are engaged each other through screws 58a and 58b.

The joined first and second substrates 26 and 42 are inserted into the cavity of the joined main body 14 and the immersion portion 16, allowing the second face 20b of the prism 20 exposed through the opening 18 of the immersion portion 16. Then the prism 20 is positioned so that the second face 20b is in the same plane as the surface 32a surrounding the opening 18. The peripheral of the second face 20b is fixed to the opening 18 by adhesive. The cap 60 is engaged with the second end 14b of the main body 14, to complete the refractometer 10.

According to the above refractometer 10, by providing an immersion portion 16 on one end of the refractometer 10 and disposing the prism 20 in the opening 18 of the immersion portion 16, the immersion portion 16 of the refractometer 10 may be immersed in a liquid for measurement (as shown in FIG. 6), instead of dripping the sample liquid onto the prism.

Figure 7:
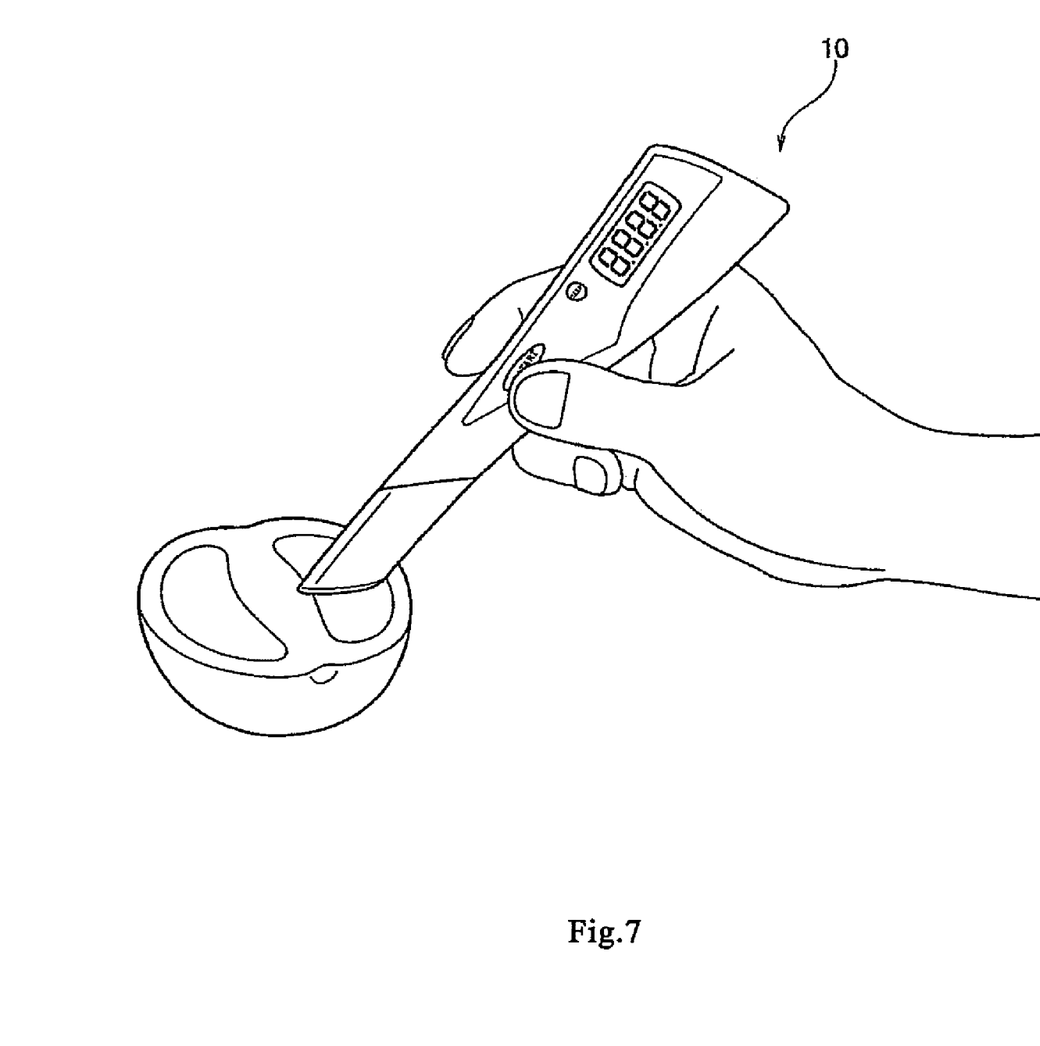
FIG. 7 shows a refractometer in contact with a cross-section of a piece of fruit, according to an embodiment of the present invention.

By disposing the face 20b of the prism 20 in the same plane as the surface 32a surrounding the prism 20, the face 20b of the prism 20 may be brought in contact with the cross-section of a fruit for measurement (as shown in FIG. 7). In such a way, the sugar content in a fruit or the like may be determined without need to squeeze juice. In addition, any sample liquid remained on the face 20b of the prism 20 and the surrounding surface 32a may be easily wiped off.

By disposing the light source 28 and the light sensor 30 on the same substrate 26, the light source 28 and the light sensor 30 may be positioned effectively. In addition, by directly jointing the first substrate 26 and the second substrate 42, the wiring of the substrates 26, 42 can be connected without electrical wires. Thus, the refractometer 10 can be manufactured more efficiently.

By disposing the light source 28 and the light sensor 30 on the same substrate 26, the position of the light source 28 and the light sensor 30 may be determined more precisely and may not need adjustment once assembled. As a result, the refractometer 10 can be more compact by eliminating space for adjusting position.

Having a substantial water-proof structure, the refractometer 10 may be cleaned as a whole. In addition, the refractometer 10 may be disposed in tubing for online measuring. When online measuring is executed, the sequential detecting mode may be selected to make multiple sequential detections.

Thus, embodiments of the present invention provide for a refractometer capable of measuring a refractive index of a liquid when immersed at least partially in the liquid. Further, embodiments of the present invention provide for a refractometer to operate by touching or bringing it into contact with a liquid bearing item, such as grocery produce.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

What is claimed is:

1. A refractometer comprising:
   a housing including an opening in an immersion portion;
   a light source configured to emit a light;
   a light sensor configured to convert a received light into an electrical signal;
   a prism including:
      a first face proximal to the light source and the light sensor;
      a second face, wherein at least a portion of the second face is configured to contact a sample liquid through the opening and to form an interface between the second face and the sample liquid; and
      a third face; and
   a control portion configured to:
      receive the electrical signal; and
      determine a refractive index of the sample liquid according to the electrical signal in at least one of a batch mode or a sequential mode,
   wherein the prism is arranged to:
      direct the light towards the second face;
      reflect the light from the interface towards the third face; and
      reflect the light from the third face towards the light sensor.

2. The refractometer of claim 1, wherein the immersion portion comprises a corrosion-resistant material.

3. The refractometer of claim 2, wherein the corrosion-resistant material comprises stainless steel.

4. The refractometer of claim 1, wherein the immersion portion comprises a surface substantially surrounding the opening, wherein the surface is substantially in a same plane as the second face.

5. The refractometer of claim 1, wherein an angle between the first face and the second face is approximately between 25 to 45 degrees.

6. The refractometer of claim 1, wherein an angle between the first face and the third face is approximately between 15 to 60 degrees.

7. The refractometer of claim 1, wherein an angle between the second face and the third face is approximately between 95 to 120 degrees.

8. The refractometer of claim 1 further comprising a substrate at least partially positioned within the housing and configured to support the light source and the light sensor.

9. The refractometer of claim 1 further comprising a display portion connected to the control portion and configured to display a representation of the refractive index.

10. The refractometer of claim 1, wherein the control portion is configured to determine the refractive index of the sample liquid in the batch mode.

11. The refractometer of claim 1, wherein the control portion is configured to determine the refractive index of the sample liquid in the sequential mode.

12. A method for measuring a refractive index of a sample liquid, the method comprising:
    contacting a sample liquid with a second face of a prism to form an interface;
    emitting a light from a light source through a first face of the prism;
    directing the light from the light source towards the interface;
    reflecting the light from the interface towards a third face of the prism;
    reflecting the light from the third face of the prism towards the first face of the prism;
    receiving the light at a light sensor;
    converting the light received at the light sensor into an electrical signal;
    receiving the electrical signal at a control portion;
    determining a refractive index of the sample liquid according to the electrical signal in at least one of a batch mode or a sequential mode.

13. The method of claim 12, wherein an angle between the first face of the prism and the second face of the prism is approximately between 25 to 45 degrees.

14. The method of claim 12, wherein an angle between the first face of the prism and the third face of the prism is approximately between 15 to 60 degrees.

15. The method of claim 12, wherein an angle between the second face of the prism and the third face of the prism is approximately between 95 to 120 degrees.

16. The method of claim 12 further comprising displaying a representation of the refractive index.

17. The method of claim 12, further comprising determining the refractive index of the sample liquid according to the electrical signal in the batch mode.

18. The method of claim 12, further comprising determining the refractive index of the sample liquid according to the electrical signal in the sequential mode.

* * * * *